(12) United States Patent
Bianchi

(10) Patent No.: US 7,025,960 B2
(45) Date of Patent: Apr. 11, 2006

(54) USE OF BETA-GLUCURONIDASE NOT IN COMBINATION WITH ALLERGENS FOR THE PREPARATION OF MEDICAMENTS FOR THE TREATMENT OF IMMUNE OR ALLERGIC DISEASES

(75) Inventor: Ines Bianchi, Grottaferrata (IT)

(73) Assignee: S.A.R.M. S.R.L., Guidonia (IT)

( * ) Notice: Subject to any disclaimer, the term of this patent is extended or adjusted under 35 U.S.C. 154(b) by 514 days.

(21) Appl. No.: 10/059,672

(22) Filed: Jan. 30, 2002

(65) Prior Publication Data

US 2002/0106365 A1    Aug. 8, 2002

(30) Foreign Application Priority Data

Jan. 31, 2001   (EP)   ................... 01830058

(51) Int. Cl.
*A61K 38/47*   (2006.01)

(52) U.S. Cl. .................... 424/94.61; 424/810
(58) Field of Classification Search ............. 424/94.61, 424/810
See application file for complete search history.

(56) References Cited

OTHER PUBLICATIONS

Di Stanislao et al., Allergy, vol. 58(5), p. 459, 2003.*

* cited by examiner

*Primary Examiner*—Patrick J. Nolan
(74) *Attorney, Agent, or Firm*—Bucknam and Archer; Joseph J. Orlando

(57) ABSTRACT

The use of beta-glucuronidase not in combination with allergens for the preparation of medicaments for the treatment of immune or allergic diseases is disclosed.

1 Claim, 1 Drawing Sheet

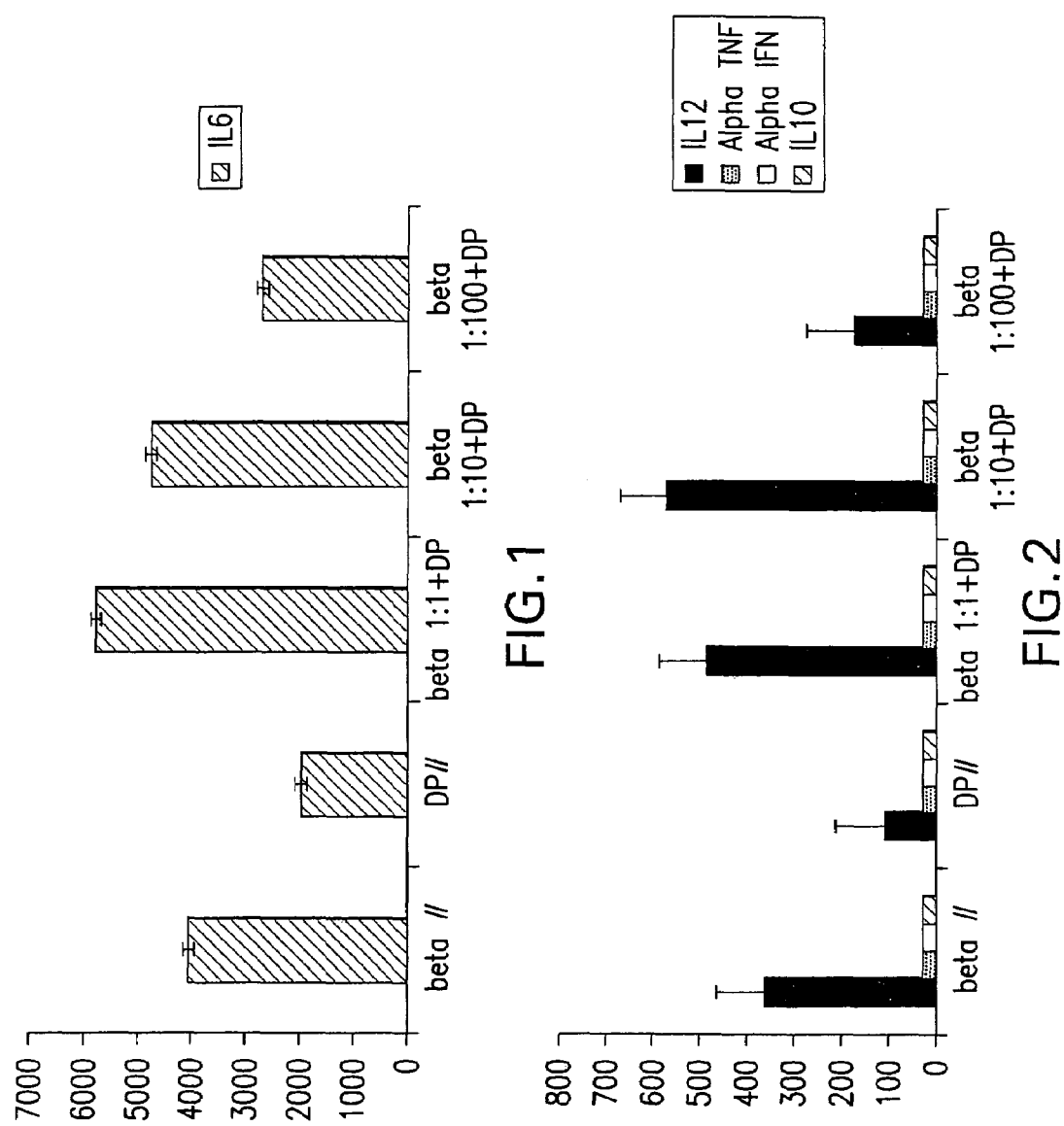

USE OF BETA-GLUCURONIDASE NOT IN COMBINATION WITH ALLERGENS FOR THE PREPARATION OF MEDICAMENTS FOR THE TREATMENT OF IMMUNE OR ALLERGIC DISEASES

FIELD OF THE INVENTION

The present invention relates to the use of the beta-glucuronidase not in combination with allergens for the preparation of medicaments for the treatment of immune or allergic diseases.

DESCRIPTION OF THE PRIOR ART

Beta-glucuronidase is a enzyme capable of cleaving glucuronic groups, present in liver, spleen, tissues of the endocrine and reproductive systems of mammals and other higher animals. The main use of beta-glucuronidase is in diagnostics, for example for the determination of steroids in blood and urine. The enzyme is also widely used as reagent in immunoenzyme and molecular biology techniques.

Recently, beta-glucuronidase inhibitors have been studied as potential drugs for the therapy of inflammatory and neoplastic diseases.

The treatment of the allergic diseases is based, on the one hand, on environmental prevention and, on the other, on the use of symptomatic medicaments and/or of specific hyposensitizing immunotherapies. The latter involve the administration of the suitably formulated allergen, responsible for the disease, at regular intervals for prolonged times (3–5 years).

A mixture of allergens and beta-glucuronidase has been commercially available for some time, which offers some advantages compared with the administration of the allergens alone.

In particular, L. M. Mc Ewen (Brit. Med. J., 1967; 11: 509–530) treated animals, which had previously been immunized with antigen plus beta-glucuronidase or hyaluronidase, and he found that these enzymes induced hyposensitization. The same Author suggested that said activity is due to the action of the enzyme on the allergen: the mixture is prepared at the time of administration, and it decreases in time, but it can be preserved by the presence of glucose. The therapeutical action is exerted by the simultaneous administration of enzyme and allergen, and it also depends on the presence of cyclohexanediol ("the ability of beta-glucuronidase and a small dose of antigen to modify 3 diol structure appears to be optimal to control the effect of the enzyme").

Subsequently, the same Author disclosed the clinical use of a product consisting of a mixture containing the enzyme, the allergen mixture, the diol and protamine (Ann. Allergy, 1973; 31: 543–550).

A number of clinical studies has subsequently been published about the effectiveness of the mixture (Feel P. et al., 1988. Eur. J. Clin. Pharmacol., 1990, 38, 77–79; Di Stanislao C, et al. Allergic et Immunologie, 1997; 2: 39–42; Vena G A, et al., The Med. J. of Surg. and Med., 1993; 253–256; Caramia G., et al., Allergie et Immunologie, 1996; 28: 70–73; Cantani A., et al J. Invest. Allergol. Clin. Immunol., 1996; 6(4): 270–276; Egger J. et al., The Lancet 1992; 2339: 1150–53; Astarita C. et al., J. Invest. Allergol. Clin. Immunol. 1996; 6 (4): 248–55; Ippoliti F. et al., Allergie et Immunologie, 1997; 29: 120–5; Troise C., et al., Allergie et Immunologie, 2000; 32: 246–49).

SUMMARY OF THE INVENTION

In any event, it is evident that beta-glucuronidase has to date been used always and only as an adjuvant or enzyme activator of allergens and not due to its own immunomodulating activity.

It has now been found that beta-glucuronidase is capable of interfering in the human immune system, as it promotes the production of cytokines, in particular of IL-12, a cytokine known to be able to shift lymphocytes from TH2 (the cause of the allergic disease) to TH1 (physiological response).

BRIEF DESCRIPTION OF THE DRAWINGS

FIG. 1 shows the concentration (pg/me) of IL-6 after treatment with beta-glucuronidase alone or in the presence of an allergen (DP); and FIG. 2 shows the concentration (pg/me) of IL-12, alpha TNF, alpha IFN and IL-10 after treatment with beta-glucuronidase alone or in the presence of an allergen (DP).

DESCRIPTION OF THE INVENTION

Therefore, the present invention relates to pharmaceutical compositions useful in the treatment of pathologies characterized by imbalanced immune system, containing beta-glucuronidase not in combination with antigens. The compositions of the invention are particularly useful in the treatment of those pathologies which can be treated or alleviated by stimulating the production of IL-12. Examples of said pathologies include all diseases which benefit from an increase in IL-12, particularly the IgE—mediated allergic ones, the most important being: asthma, rhinitis, conjunctivitis and hives.

The direct administration of IL-12 has recently been suggested as adjuvant combined with vaccines, for the treatment of viral or bacterial infections (HIV infections included), autoimmune and neoplastic diseases (WO 99/44636, WO 99/44635). The use of thalidomide to induce IL-12 production (WO 00/41547) has also been described, for the same applications.

On the other hand, Thalidomide is sadly known for its teratogenic effects, whereas the direct administration of IL-12 involves the problems connected with the use of cytokines, which are proteins difficult to dose and not free from side effects.

The use of beta-glucuronidase according to the invention is therefore advantageous and surprising, in particular compared with the above mentioned use of this enzyme in combination with the allergens, from which any activity stimulating interleukin-12 production could not be expected.

According to the invention, beta-glucuronidases of any type and origin may be used.

However, the use of a beta-glucuronidase suitably chemically modified to protect it from degradation by proteases, thereby prolonging its duration of action, is preferred. Protective techniques are well-known and comprise, for example, the introduction of polyethylene glycol residues (pegylation) or cyclohexanediol and protamine residues in the molecule.

For the envisaged for therapeutical uses, the optionally modified enzyme is suitably formulated in pharmaceutical compositions for the parenteral administration. Other administration routes, such as the oral one, can also be envisaged. Daily dosages will depend on a number of factors such as the type and severity of the disease as well as the reactivity of the immune system. As a rule, such dosages will range from about 40 U Fishman equivalents to a few μg, administered a few times at weekly or even monthly intervals.

The following example illustrates the invention in greater detail.

EXAMPLE

The activity of beta-glucuronidase on the immune system, in particular the stimulation on cytokines and specifically on interleukin 12, alpha-TNF, alpha-interferon and IL-10, was assayed. The test can be summarized as follows: CMNs were cultured in 24-wells plates ($2 \times 10^6$ cells/ml) in complete medium for 4 hours at 37° C. under humidified atmosphere enriched in 5% $CO_2$. Wells were washed 3 times with PBS, pH 7.2, the adhered cells were treated with the specific stimulus (beta-glucuronidase) and after a 3 day incubation supernatant was taken, aliquoted and stored at −20° C. until use. The amount of IL-12 was determined on each sample. The IL-12 contained in the supernatant was quantitized by ELISA (Endogen, Wobum, Mass., USA).

The results reported in the annexed figure evidence that treatment with beta-glucuronidase stimulates IL-12 production.

What is claimed is:

1. A method of treating rhinitis and conjunctivitis, the method including the administration of a pharmaceutical composition containing beta-glucuronidase not in combination with allergens.

* * * * *